United States Patent [19]

Bowley et al.

[11] 4,333,924

[45] Jun. 8, 1982

[54] RETINOL ACETATE SKIN-CARE COMPOSITIONS

[75] Inventors: Inez Bowley, Dorking; Raymond G. Harrison, Reigate, both of England

[73] Assignee: Beecham Group Limited, England

[21] Appl. No.: 133,810

[22] Filed: Mar. 25, 1980

Related U.S. Application Data

[63] Continuation of Ser. No. 933,489, Aug. 14, 1978, abandoned.

[51] Int. Cl.$^3$ .................. A61K 31/00; A61K 31/215; A61K 47/00
[52] U.S. Cl. .................................. 424/170; 424/172; 424/305; 424/344
[58] Field of Search ................ 424/305, 344, 170, 172

[56] References Cited

FOREIGN PATENT DOCUMENTS

1489133 10/1977 United Kingdom .

Primary Examiner—Leonard Schenkman
Attorney, Agent, or Firm—Jacobs & Jacobs

[57] ABSTRACT

A skin-care composition, effective in promoting epidermal mitosis, comprising from 20–40% by weight of oil, a non-ionic emulsifying agent in an amount greater than 1% by weight and retinol acetate in an amount from 1,000 to 15,000 $IUg^{-1}$. The composition preferably contains butylated hydroxytoluene or butylated hydroxyanisole as an antioxidant.

6 Claims, No Drawings

RETINOL ACETATE SKIN-CARE COMPOSITIONS

CROSS REFERENCE

This is a continuation of Ser. No. 933,489, filed Aug. 14, 1978, now abandoned.

This invention relates to topical compositions containing vitamin A acetate, such compositions being of value in the care of the skin, and being specially formulated for maximum effectiveness.

British Patent specification 1,489,133 describes and claims a liquid, semi-liquid or gel composition comprising a topically acceptable oil-in-water or water-in-oil emulsion base and retinol acetate in an amount from 1,000 to 15,000 IUg$^{-1}$, preferably 1,000 to 10,000 and more preferably 1,000 to 2,500 IUg$^{-1}$. Such compositions are of value in promoting epidermal mitosis and thus lead to a desirable thickening or "plumping" effect on the skin.

It has now been found that careful formulation of the emulsion base can lead to an unexpected increase in the effectiveness of the retinol acetate composition, resulting in high activity in skin thickening or "plumping".

Accordingly, the present invention provides a skin-care composition comprising an oil-in-water emulsion base comprising from 20–40% by weight of oil, a non-ionic emulsifying agent in an amount greater that 1% by weight and retinol acetate in an amount from 1,000 to 15,000 IUg$^{-1}$ preferably 3,000 to 6,900 IUg$^{-1}$.

It is important for maximum effectiveness that the emulsion be oil-in-water rather than water-in-oil, since tests have shown that for a given concentration of retinol acetate and similar concentration of oil (sometimes called emollient) the former produces a greater degree of epidermal thickening.

Moreover, it has been found that the effectiveness of the retinol acetate oil-in-water emulsion is greatest with oil concentrations in the range 20–40%. Thus, emulsions with oil concentrations of about 10% and about 50% oil were less effective than otherwise identical emulsions containing about 30% oil.

The further critical factor in optimising the effectiveness of the compositions of British Pat. No. 1,489,133 has been found to be the choice of emulsifier type. In order of their ability to produce skin thickening effect, anionic emulsifiers are less effective than non-ionic emulsifiers which in turn are less effective than cationic emulsifiers. However, the latter can cause skin irritation when embodied in retinol acetate compositions and are, therefore, not suitable.

It has been found that the proportion of non-ionic emulsifier in the compositions of the invention is not critical, except that at least 1% by weight is required to give a stable emulsion. However, an amount in the range 2% to 12%, preferably 4% to 8% is suitable.

Examples of oils suitable for inclusion in the present compositions include:
mineral oils, vegetable oils, synthetic fatty acid esters, fatty alcohols, lanolin and its derivatives.

Examples on non-ionic emulsifiers suitable for inclusion in the present compositions include:
sorbitan monostearate, glyceryl monostearate, polysorbates, polyethylene derivatives of fatty alcohols.

The compositions of this invention should desirably include an anti-oxidant effective in preventing oxidation of the retinol acetate and consequent reduction in the activity of the composition. Some anti-oxidants are effective in this respect but themselves oxidise to give a noticeable yellowing of the cream.

Two anti-oxidants which are particularly suitable for incorporation are butylated hydroxytoluene (BHT), correct chemical name 2,6-di-tert-butyl-p-cresol and butylated hydroxyanisole (BHA), correct chemical name 2-tert-butyl-4-hydroxyanisole or 3-tert-butyl-4-hydroxyanisole or a mixture of these. Accordingly in another of its aspects, the invention includes a composition in accordance with the invention including BHT and/or BHA as anti-oxidant.

The retinol acetate component of the compositions is preferably dispersed in the emulsion in the form of a "solubilised" mixture. Such mixtures are generally solutions of retinol acetate in hydrophilic organic solvents such as glycerine and/or propylene glycol, together with a surfactant such as "Tween 80".

The following is an example of a composition in accordance with the invention:

| FORMULA | % w/w |
| --- | --- |
| Arlacel 60 (Sorbitan Stearate) | 2.00 |
| Tween 60 (Polysorbate 60) | 2.00 |
| Cetyl alcohol | 2.00 |
| Emulgade F (Emulsifying Wax) | 2.50 |
| Mineral Oil | 25.00 |
| Lanolin | 2.50 |
| Cetiol V (Decyl Oleate) | 2.00 |
| Preservatives | 0.37 |
| Anti-oxidant (BHT) | 0.20 |
| Perfume | 0.45 |
| Water soluble retinol acetate* | 3,000–7,000 IUg$^{-1}$ |
| Deionised water | to 100.00 |
| *Retinol acetate 1 × 10$^6$ IUg$^{-1}$ | 10.00 |
| Tween 80 ("Tween" is a Registered Trade Mark) | 50.00 |
| Glycerine | 15.00 |
| Propylene glycol | 15.00 |
| Water | to 100.00 |

We claim:

1. A skin care composition comprising an oil-in-water emulsion base comprising about 30% by weight of an oil selected form the group consisting of mineral oil and mineral oil in combination with lanolin and decyl oleate, a non-ionic emulsifying agent in an amount from 2 to 12% by weight and retinol acetate in an amount from 1,000 to 15,000 IUg$^g-1$.

2. A composition according to claim 1 which contains 3,000 to 6,900 IUg$^{-1}$ retinol acetate.

3. A composition according to claim 1 which contains from 4 to 8% by weight of non-ionic emulsifying agent.

4. A composition according to claim 1 wherein the non-ionic emulsifier is selected from the group consisting of sorbitan monostearate, glyceryl monostearate, polysorbates and polyethylene derivatives of fatty alcohols.

5. A composition according to claim 1 which additionally contains butylated hydroxytoluene or butylated hydroxyanisole as an antioxidant.

6. A composition according to claim 1 wherein the retinol acetate is incorporated as a solution in a hydrophilic organic solvent additionally containing a surfactant.

* * * * *